United States Patent [19]

Fogarty et al.

[11] Patent Number: 4,775,379
[45] Date of Patent: Oct. 4, 1988

[54] SELF-SEALING VALVE FOR FLUID FILLABLE ARTICLE

[75] Inventors: Terence M. Fogarty, Hudson, Wis.; Hilton Becker, Boca Raton, Fla.

[73] Assignee: Mentor Corporation, Minneapolis, Minn.

[21] Appl. No.: 947,736

[22] Filed: Dec. 30, 1986

[51] Int. Cl.⁴ ............................................. A61F 2/12
[52] U.S. Cl. ........................................ 623/8; 138/118
[58] Field of Search ............... 623/8, 11, 7; 137/846, 137/223; 251/149; 138/118

[56] References Cited

U.S. PATENT DOCUMENTS

| | | | |
|---|---|---|---|
| 564,502 | 7/1896 | Brookes . | |
| 1,008,641 | 11/1911 | Gregory . | |
| 1,551,099 | 8/1925 | Goldsmith et al. . | |
| 2,142,414 | 1/1939 | Riddell | 273/65 |
| 2,516,129 | 7/1950 | Leo et al. | 2/42 |
| 2,568,976 | 9/1951 | Andrews | 251/119 |
| 2,697,229 | 12/1954 | Krueger | 2/267 |
| 2,700,980 | 2/1955 | Andrews | 137/233 |
| 2,795,425 | 6/1957 | Orms | 273/58 |
| 2,826,523 | 3/1958 | Blaszkowski . | |
| 2,933,120 | 4/1960 | Siedow | 152/429 |
| 3,204,959 | 9/1965 | Nicholls | 273/58 |
| 3,410,300 | 12/1968 | Mondano | 137/223 |
| 3,523,563 | 8/1970 | Mirando | 141/313 |
| 3,565,078 | 2/1971 | Valliancourt | 128/349 |
| 3,584,672 | 6/1971 | Kampa | 152/429 |
| 3,600,718 | 8/1971 | Boone | 623/8 |
| 3,852,832 | 12/1974 | McGhan et al. | 623/8 |
| 3,852,833 | 12/1974 | Koneke et al. | 623/7 |
| 3,883,902 | 5/1975 | Lynch | 3/36 |
| 3,939,875 | 2/1976 | Osborn et al. | 138/178 |
| 4,178,643 | 12/1979 | Cox, Jr. | 623/7 |
| 4,263,682 | 4/1981 | Bejarano | 3/36 |
| 4,433,440 | 2/1984 | Cohen | 623/8 |
| 4,459,318 | 7/1984 | Hyans | 427/36 |
| 4,662,883 | 5/1987 | Bell et al. | 623/8 |

FOREIGN PATENT DOCUMENTS 9698 of 1902 United Kingdom ............... 137/223

Primary Examiner—John D. Yasko
Attorney, Agent, or Firm—Kinney & Lange

[57] ABSTRACT

A valve for use in a fluid fillable device includes a main body portion movable from a fluid position to a curled fluid sealing position. The main body portion includes a sealing section made of an elastomeric material and having a passage portion defining a passage for receiving a fill tube. The passage portion is flanked on opposing sides by first and second portions of elastomeric material. The passage portion is in a stretched state relative to the first and second portions, such that the passage portion curls along the passage when the fill tube is removed.

24 Claims, 4 Drawing Sheets

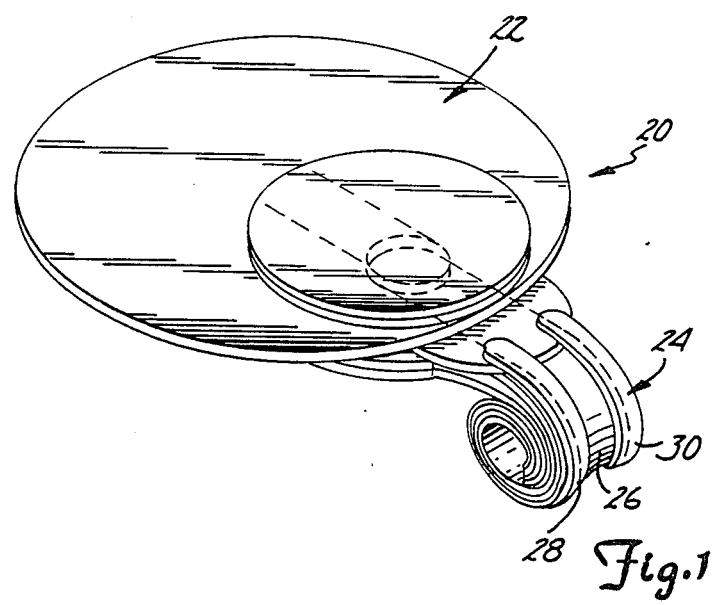
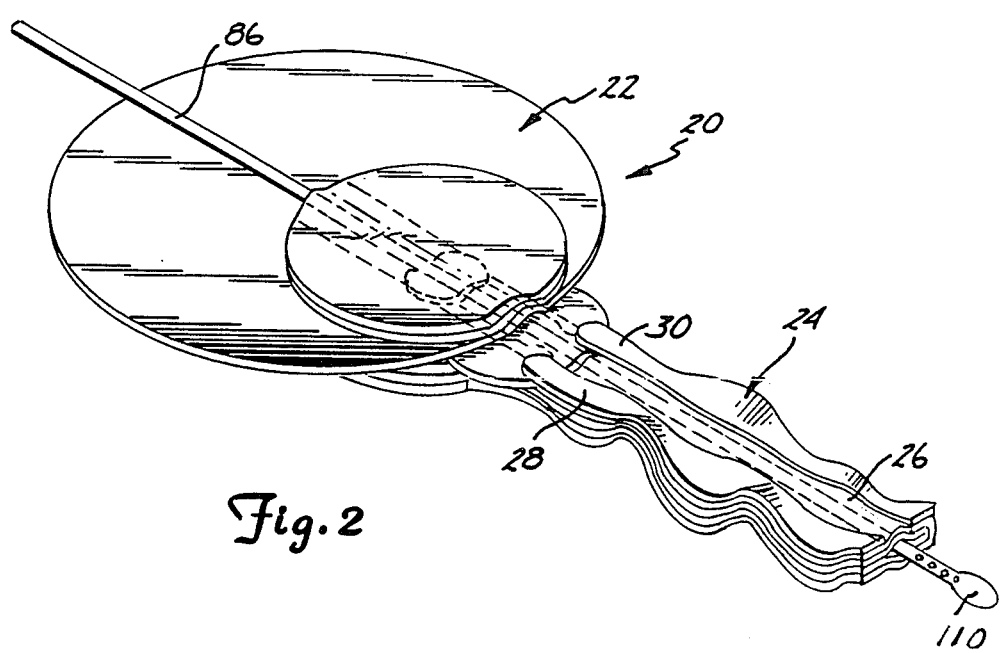

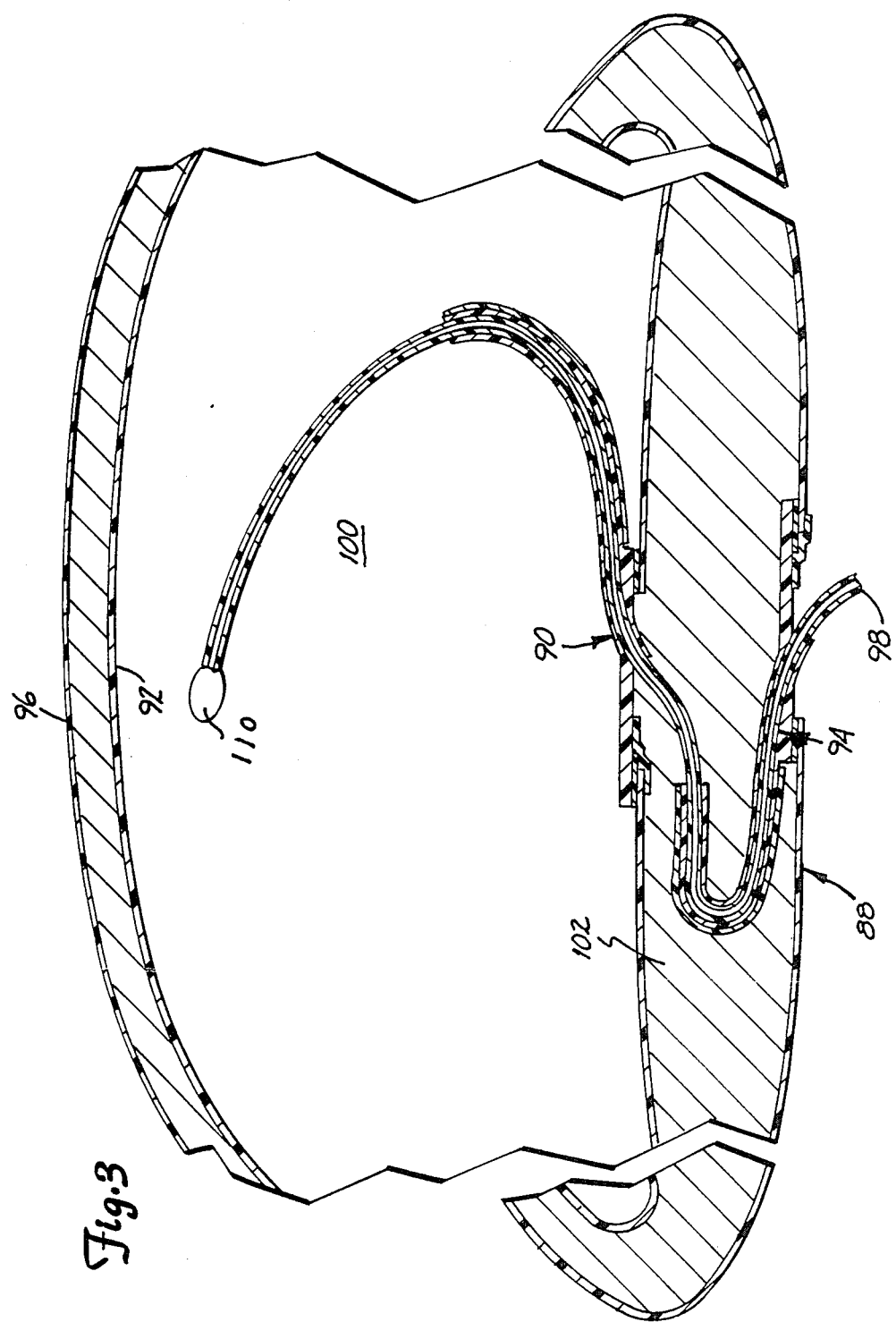

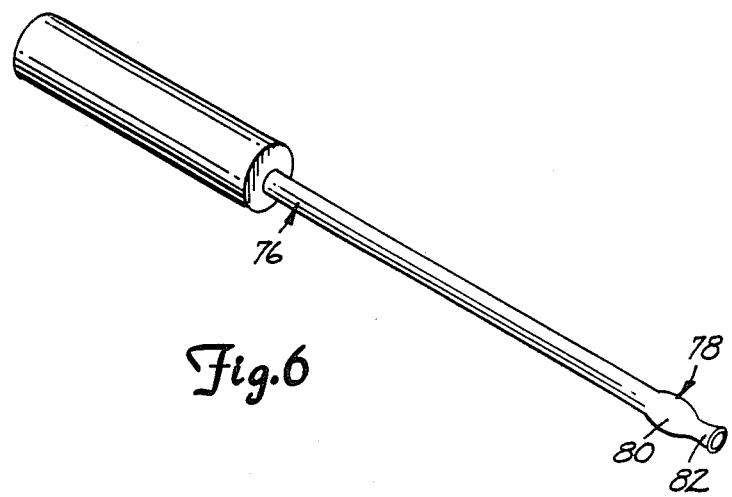
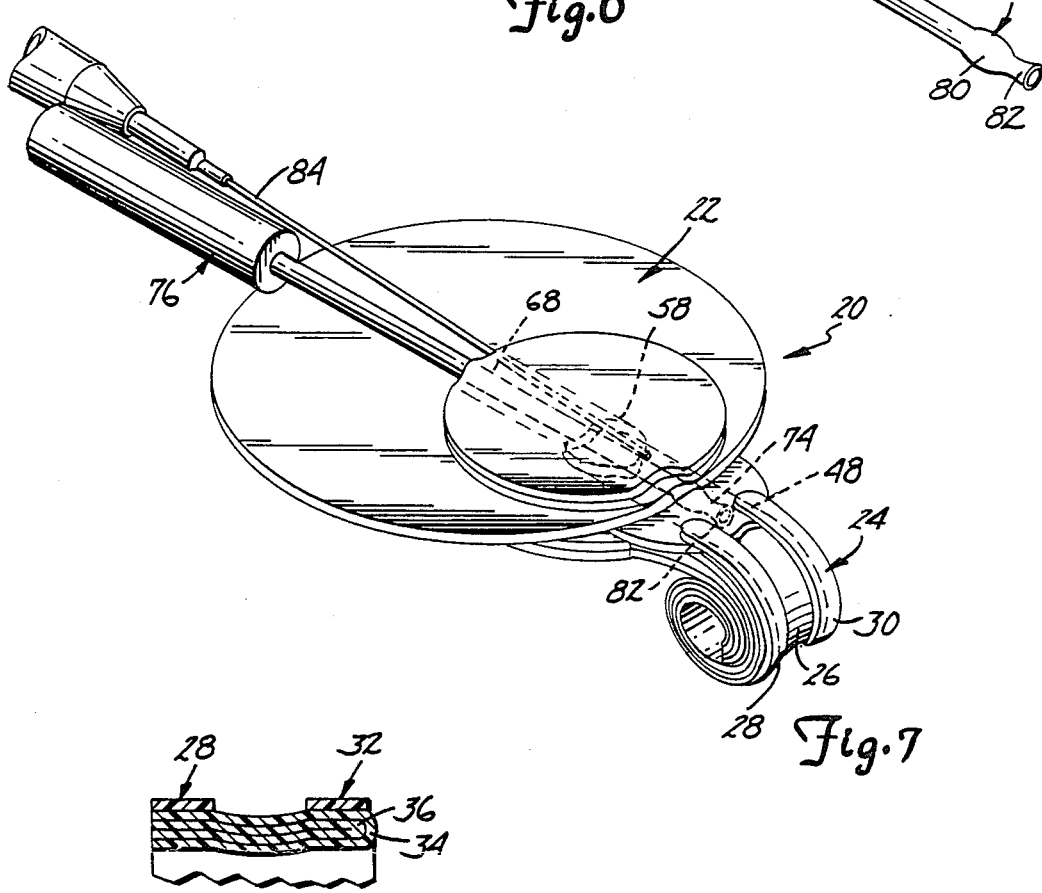

SELF-SEALING VALVE FOR FLUID FILLABLE ARTICLE

REFERENCE TO CO-PENDING APPLICATION

Reference is hereby made to a co-pending patent application assigned to the same assignee as the present application entitled, "Self-Sealing Valve for Fluid Fillable Device," filed on July 17, 1985 under Ser. No. 756,408, now U.S. Pat. No. 4,662,883; and to a co-pending patent application entitled, "Improved Implant and Inflating Construction," filed on Jan. 23, 1985 under Ser. No. 693,890.

BACKGROUND OF THE INVENTION

1. Field of the Invention

The present invention relates to self-sealing valves, and in particular, it relates to self-sealing valves for use in inflatable devices.

2. Description of the Prior Art

In recent developments in inflatable prosthetic devices, it has been found desirable to progressively inflate the prosthetic device over a period of time. This has required the use of subcutaneous injection sites connected to the inflatable prosthetic device by a fill tube. In addition, mammary prostheses having an inner chamber disposed within an outer chamber with the two chambers being filled with dissimilar fluids have become popular. Typically, the outer chamber is filled with a silicone gel prior to implantation and after the prosthesis has been implanted, a fill tube which extends through a valve in the outer chamber, through the outer chamber, and into the inner chamber through a second valve is used to fill the inner chamber with a saline solution.

The valve is typically made of two sheets of silicone rubber bonded together along their edges with a passage therebetween. If a fill tube is disposed within the valve for a long time, stresses in the silicone rubber forming the passage result in the valve not sealing adequately once the fill tube is removed. The passage becomes somewhat "set" in an open position and remains in the set open position once the fill tube has been removed.

A curling self-sealing valve is described in patent application Ser. No. 756,408, now U.S. Pat. No. 4,662,883, entitled, "Self-Sealing Valve for Fluid Fillable Device," filed on July 17, 1985, and assigned to the same assignee as the present application, provides a seal by curling along the longitudinal axis of the fill tube passage. This device has been on sale for more than one year prior to the filing date of the present application.

A number of patents directed to prosthetic inflatable devices show valves which are constructed of two sheets of silicone elastomer bonded together along two edges to form a passage. None of the valves illustrated in the immediately below-listed patents are constructed to avoid the passage being permanently deformed due to the stress caused on the material by the fill tube inserted into the passage over a long period of time:

| Inventor | U.S. Pat. No. |
| --- | --- |
| Hyans | 4,459,318 |
| Bejarano | 4,263,682 |
| Cox, Jr. | 4,178,643 |
| Koneke et al | 3,852,833 |
| McGhan et al | 3,852,832 |
| Valliancourt et al | 3,565,078 |
| Krueger | 2,697,229 |

The Lynch U.S. Pat. No. 3,883,902 and the Boone U.S. Pat. No. 3,600,718 show other types of valves used in inflatable prosthetic devices. The valve illustrated in the Lynch Patent shows a complicated sealing arrangement and the valve shown in the Boone Patent shows a valve using a silicone gel chamber as a sealing arrangement.

Still other patents show inflatable devices other than prosthetic devices using a variety of valving arrangements for the introduction of air. However, similar to the patents directed to prosthetic devices, the valves shown in the immediately below-listed patents are also not designed for the retention of a fill tube for a long period of time.

| Inventor | U.S. Pat. No. |
| --- | --- |
| Kampa | 3,584,671 |
| Mirando | 3,523,563 |
| Mondano | 3,410,300 |
| Nicholls | 3,204,959 |
| Siedow | 2,933,120 |
| Orms | 2,795,425 |
| Andrews | 2,568,976 |
| Goldsmith et al | 1,551,099 |
| Foreign Patents | |
| Inventor (Country) | Patent No. |
| Ingram (British) | 9,698 |

SUMMARY OF THE INVENTION

The present invention includes a valve for use in the fluid fillable devices, such as devices that are suitable for implantation into the human body. The valve includes a main body portion made of an elastomeric material and movable from a fluid flowable position to a curled fluid sealing position. The main body portion includes a sealing section having a passage portion defining a passage for receiving a fill tube. The passage portion is flanked on opposing sides by first and second portions of elastomeric material with the passage portion being in a stretched state relative to the first and second portions such that the passage portion curls on itself when the fill tube is removed.

In a preferred embodimemt, the valve is constructed of a layer of a silicone elastomer having a low tension set property in the range of 4% to 8% and a layer of silicone elastomer having a high tension set property of 12% to 20%.

BRIEF DESCRIPTION OF THE DRAWINGS

FIG. 1 is perspective view of the valve of the present invention in a curled state.

FIG. 2 is a perspective view of the valve of the present invention in an uncurled state.

FIG. 3 is a cross-sectional view of a mammary prosthesis using the valve of the present invention.

FIGS. 4–7 are perspective views illustrating a manner of making the valve of the present invention.

FIG. 8 is a cross-sectional view of the sealing portion of the valve of the present invention.

DETAILED DESCRIPTION OF THE PREFERRED EMBODIMENTS

Figure 4:
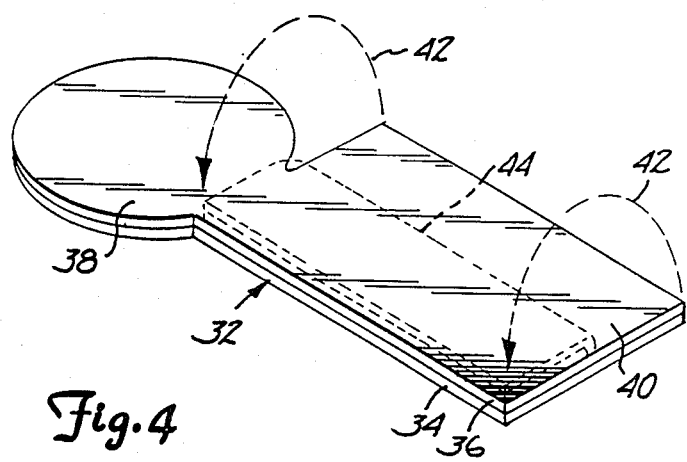

The valve of the present invention is generally indicated at 20 in FIGS. 1 and 2. The valve 20, illustrated in FIG. 1, is in a curled or fluid sealing position. The valve illustrated in FIG. 2 is in an uncurled or fluid fillable position. The valve 20 is used to introduce fluid into an implantable prosthesis, such as a mammary prosthesis illustrated in FIG. 3. The valve is useful for introducing fluid in other implantable devices such as tissue expanders and penile prostheses. The valve is capable of holding a hydrostatic pressure while accommodating a fill tube, cannular or stylet.

The valve 20 of the present invention is an improved valve structure over the valve structure described in patent application Ser. No. 756,408, now U.S. Pat. No. 4,662,883, entitled "Self-Sealing Valve for Fluid Fillable Device," of Julie D. Bell et al, filed on July 17, 1985, assigned to the same assignee as the present application and which is herein incorporated by reference; and the valve structure described in patent application Ser. No. 693,890 entitled "Improved Implant and Inflating Construction," of Dr. Hilton Becker, filed on Jan. 23, 1985, which is also herein incorporated by reference. The valve described in application Ser. No. 06/756,408, now U.S. Pat. No. 4,662,883, was a first workable example of a curled valve suitable for inflatable implantation devices. However, there have been some problems with the valve leaking saline solution in mammary prostheses, especially when the mammary prostheses were stored for long periods of time with the valve being in the uncurled state with the fill tube. It was found that when such prostheses were stored for an extended period of time, the valve did not immediately curl to a fluid sealing position after the fill tube was removed. In addition, the valve did not curl to a position that was sufficient to provide a satisfactory seal for saline solution.

In the present invention, it is believed that the problem caused by a curled leaf valve in the uncurled state for an extended period of time results from "creep". By "creep" is meant the phenomena through which an elastomer loses its ability to return to its unstressed or original position. To overcome the occurence of "creep", the valve of the present invention is constructed of sheets of elastomers having dissimilar properties, which are discussed subsequently. The valve is constructed using sections of calendered sheeting which enable elastomers of different characteristics or properties to be incorporated in different sections of the valve.

Referring back to FIGS. 1 and 2, the valve of the present invention includes an inlet portion 22 and a sealing portion 24. The sealing portion 24 includes a passage section 26 and first and second curling strip sections 28 and 30 disposed adjacent to the passage section on opposing sides. Further details of the valve structure of the present invention are best understood by describing the manner in which the valve is constructed.

Referring to FIG. 4, a valve blank 32 made of a first layer 34 of a vulcanized low tension set silicone elastomer and a second layer 36 of an unvulcanized high tension set elastomer is illustrated. The layers 34 and 36 are preferably die cut or punched from calendered sheets of elastomer.

By a low tension set elastomer is meant an elastomer such as a silicone elastomer sold by Dow Corning under the designation of MDX-4-4515, which is a 50 durometer silicone elastomer having a tension set property of 4% to 8%, a tensile modulus of elasticity of 300 psi at 200% elongation and 600 psi at 300% and an elongation of 400%. Tension set was determined by using a modified ASTM D412 test at 300% elongation. The modification included holding the elastomer at the stretched position for 15 seconds and then in a relaxed position at 15 seconds, instead of 10 minutes, as called for by the test. Such an elastomer has excellent "memory", that is, the elastomer tends to return to its original shape even though the elastomer has been placed under stress for extended periods of time. This type of an elastomer has outstanding properties against "creep".

By the term high tension set elastomer is meant an elastomer such as a silicone elastomer sold by Dow Corning under the designation Q7-2174 which is a 50 durometer elastomer having a tension set property of 12% to 20%, a tensile modulus of elasticity of 525 psi at 200% elongation and 850 psi at 300% elongation and an elongation of 725%. Such an elastomer has poor "memory" characteristics and is an excellent material for adhering vulcanized layers of silicone elastomer. Such an elastomer yields at a bonding interface with the vulcanized elastomer and acts as an absorber of stresses when bonded to the vulcanized elastomer.

The valve blank 32 includes a circular portion 38 which will form an inlet passage to the sealing portion, as will be described subsequently, and a generally rectangular section 40 which will form the sealing portion. As illustrated in FIG. 4, the generally rectangular section 40 is folded on itself, as generally shown by arrows 42 and broken lines 44 such that the unvulcanized high tension set elastomer contacts itself. When the valve is vulcanized, the folded layers will bond to each other and will bond to the vulcanized layers to form the sealing portion.

Figure 5:
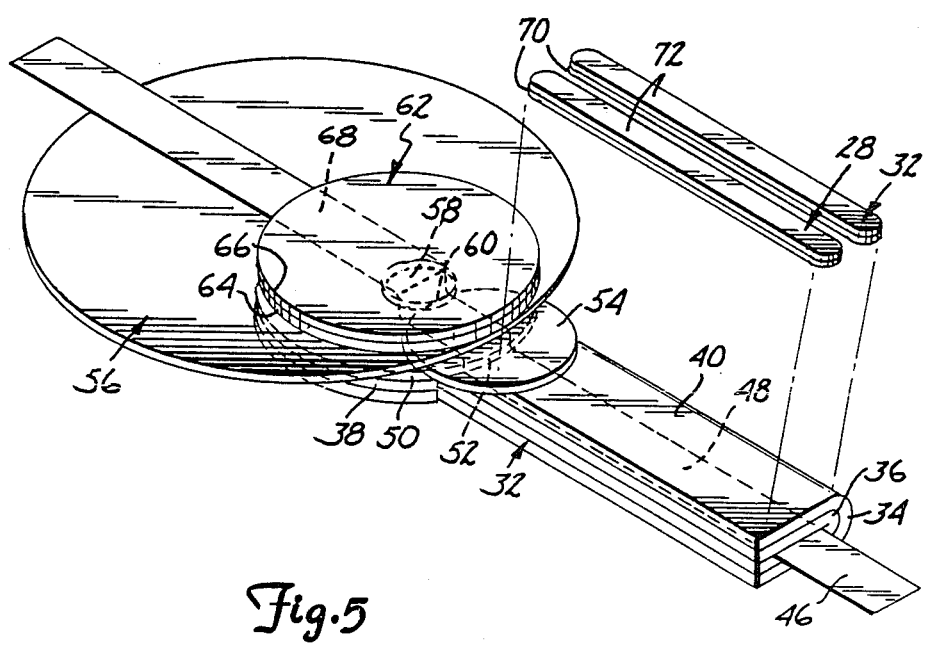

Referring to FIG. 5, an approximately 0.0005 inches thick Teflon ® ribbon 46 is positioned between the unvulcanized high tension set elastomeric folded layers 36 to form a passage 48. The ribbon 46 is centrally located along the longitudinal axis of the generally rectangular folded-over section 40 and disposed centrally over the circular section 38. The Teflon ® ribbon 46 will not adhere to the silicone elastomer during vulcanization and will permit the elastomer to cure without touching adjacent surface sections thereby forming the passage 48.

A high tension set unvulcanized elastomeric washer 50 having generally the same diameter as the circular section 38 is disposed thereon with a portion 52 extending over the top surface of the rectangular section 40. A second smaller washer 52 of a high tension unvulcanized elastomer is disposed such that approximately one-half the area of the washer 52 extends over the top surface of the rectangular section 40 and the other half of the washer 52 extends over a top surface of the washer 50. For purposes of illustrating the comparative sizes of the washers 50 and 52, in one working embodiment, the washer 50 was approximately 0.75 inches in diameter while the washer 52 was approximately 0.59 inches in diameter.

On top of the washers 50 and 52 is placed a vulcanized prosthesis plug 56 made of a high tension set vulcanized silicone elastomer having an aperture 58.

The ribbon 46 extends through the aperture 58 at an inner edge 60 of the washer 54.

It has been found that a minimum thickness of approximately 0.020 inches of unvulcanized silicone is needed to achieve a minimum bonding between the vulcanized layers of silicone. Therefore, the layer 36 is approximately 0.010 inches thick and when folded over on itself is approximately 0.020 inches thick. The reason for the phenomenon is not fully understood. It is believed that such a thickness is needed for the high tension set layers to absorb the stresses that the valve is subjected to. This is one reason that the washers 50 and 54 are included. The washer 50 adds an additional approximately 0.010 inches of unvulcanized high tension set elastomer to the layer of high tension set elastomer in the circular section 38. The washer 52 adds an additional approximately 0.010 inches of unvulcanized elastomer over the top surface of the Teflon ® ribbon and over a portion of the rectangular section which forms the sealing portion of the valve to act as a strain absorbing segment when the valve is subsequently attached to a prosthesis.

A third top washer 62 includes a lower layer of unvulcanized high tension set silicone elastomer 64 and a top layer 66 of a vulcanized low tension set elastomer. The washer 62 is disposed on top of the plug 56. A portion 68 of the ribbon 46 that extends above the opening 58 is disposed between the plug 56 and the lower layer 64 of the washer 62 to form an inlet passage for the fill tube.

The entire subassembly, as described above, is vulcanized in a conventional manner and then post-cured in a conventional manner. After post-curing, the Teflon ® ribbon 46 is removed with a radius stylet, using alcohol to swell the silicone and lubricate the Teflon ® ribbon.

The section 40 is then stretched to approximately 150% of its original length. While the section 40 is stretched, the curling strips 28 and 32 are positioned along opposing edges of the passage 48, as best illustrated in FIGS. 1, 2 and 8. The curling strips 28 and 32 are each made of two layers of silicone elastomer, with the lower layer 70 made of a high tension set unvulcanized silicone elastomer and the top layer 72 being mase of a low tension set vulcanized silicone elastomer. The lower layer 70 is placed in contact with the vulcanized layer 34 for bonding of the strips to the section 40. The placement of the curl strips, that is on both sides of the passage 48, causes the passage section of the valve to curl along the longitudinal axis of the passage, as illustrated in FIG. 1, and to also curl in a direction perpendicular to the axis of the passage, as illustrated in FIG. 8, forcing the layers that define the passage 48 toward each other. As illustrated in FIG. 8, a cross-sectional view of the sealing portion of the valve shows the passage 48 having a concave cross-sectional configuration. The curling strips are then vulcanized to the rectangular section 40, thereby forming the sealing portion of the valve 20 of the present invention.

Stretching the section 40 thins out the layers forming the passage 48, thereby making the passage section more compliant than the passage section of the valve described in application Ser. No. 756,408, now U.S. Pat. No. 4,662,883. A more compliant passage section results in a better sealing of the passage when the valve is in the curled position. After vulcanization, the valve assembly is released from its stretched position, and post-cured in a conventional manner.

To further ensure sealing of the valve, a room temperature vulcanizing (RTV) silicone elastomer is injected in the passage between the opening 58 and the curling strips 28 and 32 to form a sealing insert. To position the RTV silicone elastomer in the passage, a Teflon ® pin 76, as illustrated in FIG. 6, is inserted within the passage 68, through the opening 58, and into the passage 48. The pin 76 has a distal portion 78 with a bulbous section 80 necking down and continuing into a frusto-conical end portion 82. The Teflon ® pin at its narrowest point between the frusto-conical end portion 82 and the bulbous section 80 has a diameter that is 10% smaller than the external diameter of the fill tube.

The pin 76 is positioned such that the frusto-conical end portion 82 is disposed just past the curling strips 28 and 32. RTV elastomer is injected using a cannula-type tool 84 so that the RTV elastomer is injected around the frusto-conical end portion 82 of the pin, with the bulbous portion 80 and the end of the frusto-conical portion 82 preventing the elastomer from flowing out of the desired area. The RTV elastomer occupies approximately a one-quarter inch ($\frac{1}{4}$") to one-half inch ($\frac{1}{2}$") distance within the passage 48. The RTV elastomer is allowed to thoroughly cure while the pin is still within the passage. After curing, the pin is removed. Curing takes approximately 72 hours. The RTV forms a sealing insert whose cross-sectional shape is somewhat the shape of a Chevron that engages the exterior surface of the fill tube and prevents fluid from leaking through the passage while the fill tube is in the valve channel. Prevention of fluid leaking while the valve is in the uncurled state is important when the valve is used in a prosthesis that is inflated over an extended period of time, such as a skin expander or a skin expander/mammary prosthesis.

After the RTV elastomer has cured, a silicone gel is injected into the channel, for example, approximately 0.1 gram of Dow Corning Q7-2167-68 gel and permitted to cure for 2 hours ±15 minutes at 325° F.±10° F. The silicone gel, upon curing, bonds to the elastomer at the surface defining the passage 48. In addition, the gel softens and swells the surfaces of the passage 48 enhancing the sealing characteristics of the valve. In addition, the silicone gel acts as a lubricant between the fill tube, facilitating insertion and removal of the fill tube from the passage.

The fill tube has a bulbous end 110. The bulbous end 110 is attached to the tubing at a selected tension load that causes the end 110 to break from the tubing when engaging the sealing insert and acts as a plug. The bulbous end becomes lodged in the insert due to the tapered surface engaging the insert. The bulbous end acts as an additional barrier to stop biological or tissue ingrowth into the valve passage.

A fill tube 86, as illustrated in FIG. 2, is inserted into the passage to place the valve in a fluid fillable position. As the tube is inserted into the passage 48, the sealing portion uncurls.

When the fill tube is removed from the valve, the valve will assume a curled or sealed position, as illustrated in FIG. 1.

In FIG. 3, a double-chambered mammary prosthesis, generally indicated at 88, includes a first valve 90 of the present invention attached to an inner shell 92, and a second valve 94 of the present invention attached to an outer shell 96. A fill tube 98 extends through the valve 94, and 90, providing access for fluid to flow into an interior chamber 100 of the inner shell 92. An outer chamber 102 is defined by the inner and outer shells 92 and 96 and is filled with a silicone gel 102. A saline solution is then introduced into the inner chamber 100 through the fill tube 98.

In implanting the breast prosthesis illustrated in FIG. 3, the prosthesis is implanted with the inner chamber empty of fluid. Once the prosthesis is implanted, saline solution is introduced into the inner chamber, inflating the prosthesis to a selected size. Once the prosthesis is inflated, the fill tube 98 is pulled out of the valve 90 and the valve 94, with the valves 90 and 94 curling into a fluid sealing position, sealing the inner chamber 100 and the outer chamber 102 permanently.

The valve of the present invention may function as part of a permanent implant with the fill tubing present in the valve indefinitely, or, if required, as in the double-chambered mammary prosthesis described above, the tubing may be removed. In some cases, it is desirable to provide an excess amount of tubing in the prosthesis. The excess amount of tubing provides the surgeon with a sufficient length of tubing so that the length of tubing exiting the prosthesis may be adjusted to a desired length by simply pulling the amount of tubing desired through the valves of the prosthesis.

Furthermore, the valve of the present invention prevents leaking of saline solution from the inner chamber while the tubing is disposed within the valve. Preventing leaking of saline solution through the passage while the tube is in the valve is important when the valve is used in prostheses that are expanded over a period of time, such as skin expanders.

In addition, the valve of the present invention curls immediately once the fill tube is removed due to the unique construction of the valve, preventing loss of fluid from the chamber. The valve of the present invention permits factory installation of the fill tube since the prosthesis may then be stored with the fill tube in the valve for extended periods of time. This is important when the prosthesis contains multiple chambers with multiple valves controlling flow within each of the chambers. It is desirable that such prosthesis have the fill tube installed at the factory.

Although the present invention has been described with reference to peferred embodiments, workers skilled in the art will recognize that changes may be made in form and detail without departing from the spirit and scope of the invention.

What is claimed is:

1. An improved valve for use in a fluid fillable device, the valve including a main body portion, the main body portion having a sealing section for controlling fluid flow through the main body, the sealing section being movable from a fluid flowable position to a curled fluid sealing position, the improvement comprising:

the sealing section having a passage portion defining a passage for receiving a fill tube, the sealing section further including a layer of unstretched low tension set elastomer bonded to a layer of stretched low tension set elastomer by a layer of high tension set elastomer, the bonded layers forming at least a portion of the sealing section along both sides of the passage such that the passage portion curls on itself along the axis of the passage when the fill tube is removed.

2. The valve of claim 1 wherein a restriction is disposed within the passage for engaging an exterior surface of the fill tube providing a fluid seal while the fill tube is within the passage.

3. The valve of claim 1 wherein the passage is coated with a silicone gel.

4. The valve of claim 3 wherein the silicone gel has been cured.

5. The valve of claim 1 wherein the passage portion has a concave cross-sectional configuration.

6. The valve of claim 1 wherein the passage portion was initially stretched approximately 150%.

7. An implantable device comprising:
an expandable envelope defining a fluid fillable chamber; and
valve means attached to the envelope and for controlling fluid flow to the envelope, the valve means having a sealing section being movable from a fluid flowable position to a curled fluid sealing position, the sealing section having a passage portion defining a passage for receiving a fill tube, the sealing section further including a layer of unstretched low tension set elastomer bonded to a layer of stretched low tension set elastomer by a layer of a high tension set elastomer, the bonded layers forming at least a portion of the sealing section on both sides of the passage such that the passage portion curls on itself along the axis of the passage when the fill tube is removed.

8. The device of claim 7 wherein a restriction is disposed within the passage for engaging an exterior surface of the fill tube providing a fluid seal while the fill tube is within the passage.

9. The device of claim 7 wherein the passage is coated with a silicone gel.

10. The device of claim 9 wherein the silicone gel has been cured.

11. The device of claim 7 wherein the passage portion has a concave cross sectional configuration.

12. The device of claim 7 wherein the passage portion was initially stretched approximately 150%.

13. An implant device comprising:
outer shell means;
inner shell means disposed within the outer shell means for filling with a first inflatable fluid;
a second fluid being disposed between the inner and outer shell means;
first valve means positioned on the outer shell means for providing fluid flow into and through the outer shell means; and
second valve means positioned on the inner shell means providing access to the inner shell means, the second valve means having a sealing section being movable from a fluid flowable position to a curled fluid sealing position, the sealing section having a passage portion defining a passage for receiving a fill tube extending from the first valve means to the second valve means providing fluid communication, the sealing section further including a layer of unstretched low tension set elastomer bonded to a stretched layer of a low tension set elastomer by a layer of a high tension set elastomer, the bonded layers forming at least a portion of the sealing section along opposite sides of the passage such that the passage portion curls on itself along the axis of the passage when the fill tube is removed.

14. The device of claim 13 wherein a restriction is disposed within the passage for engaging an exterior surface of the fill tube providing a fluid seal while the fill tube is within the passage.

15. The device of claim 13 wherein the passage is coated with a silicone gel.

16. The device of claim 15 wherein the silicone gel has been cured.

17. The device of claim 13 wherein the passage portion has a concave cross sectional configuration.

18. The device of claim 13 wherein the passage portion was initially stretched approximately 150%.

19. The device of claim 13 wherein the first valve means has a sealing section being movable from a fluid flowable position to a curled fluid sealing position, the sealing section having a passage portion defining a passage for receiving a fill tube, the sealing section further including a layer of unstretched low tension set elastomer bonded to a layer of stretched low tension set elastomer by a layer of a high tension set elastomer, the bonded layers forming at least a portion of the sealing section along opposite sides of the passage such that the passage portion curls on itself along the axis of the passage when the fill tube is removed.

20. The device of claim 19 wherein a restriction is disposed within the passage for engaging an exterior surface of the fill tube providing a fluid seal while the fill tube is within the passage.

21. The device of claim 19 wherein the passage is coated with a silicone gel.

22. The device of claim 21 wherein the silicone gel has been cured.

23. The device of claim 19 wherein the passage portion has a concave cross sectional configuration.

24. The device of claim 19 wherein the passage portion was initially stretched approximately 150%.

* * * * *